(12) United States Patent
Huang et al.

(10) Patent No.: US 8,291,774 B2
(45) Date of Patent: Oct. 23, 2012

(54) STRESS TEST APPARATUS FOR HINGE

(75) Inventors: Teng-Tsung Huang, Taipei Hsien (TW);
Guo-Jun Yu, Shenzhen (CN);
Yong-Bing Hu, Shenzhen (CN);
Yuan-Zhao Li, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu Cheng, New Taipei (TW)

( * ) Notice: Subject to any disclaimer, the term of this patent is extended or adjusted under 35 U.S.C. 154(b) by 277 days.

(21) Appl. No.: 12/889,555

(22) Filed: Sep. 24, 2010

(65) Prior Publication Data

US 2011/0277561 A1    Nov. 17, 2011

(51) Int. Cl.
*G01L 3/02* (2006.01)
(52) U.S. Cl. .................................................. 73/862.191
(58) Field of Classification Search .............. 73/862.191
See application file for complete search history.

(56) References Cited

U.S. PATENT DOCUMENTS 2,300,288 A * 10/1942 Hullhorst ................. 73/862.191
6,381,809 B2 * 5/2002 Uneme et al. .................... 16/342

* cited by examiner

*Primary Examiner* — Lisa Caputo
*Assistant Examiner* — Octavia Davis-Hollington
(74) *Attorney, Agent, or Firm* — Altis Law Group, Inc.

(57) ABSTRACT

A stress test apparatus used for testing torque between a top portion and a bottom portion of an electronic device. The stress test apparatus includes a console, a rotary table, a lifting pole, a traversing arm, a securing fixture and torque sensor. The rotary table is located on the console for retaining the bottom portion. The lifting pole extends from the console. The traversing arm is gearingly engaged to the lifting pole to adjust a height of the traversing arm relative to the console. The securing fixture clasps the top portion of the electronic device. The torque sensor is fixed between the traversing arm and the securing fixture. The bottom portion is rotated relative to the top portion with rotation of the rotary table, and the torque sensor is capable of detecting needed for rotating the top portion relative to the bottom portion.

20 Claims, 9 Drawing Sheets

STRESS TEST APPARATUS FOR HINGE

BACKGROUND

1. Technical Field

The present disclosure relates to a stress test apparatus for a hinge of an electronic device.

2. Description of Related Art

Many electronic devices such as notebook computer, mobile phones have hinges. The hinges of the electronic devices must pass a stress test before placed into practical application. However, after assembled, the components of an electronic device may not perform according to specification because of wear and tear in the production line. For example, a hinge, prior to assemble on an electronic device, passes all tests, however, after complete assemble of the electronic device, movement of the hinge may appear tighter or looser. Thus, the hinge, inter alia, of the electronic device needs to be tested before they are shipped to the consumers. Therefore there is room for improvement in the art.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
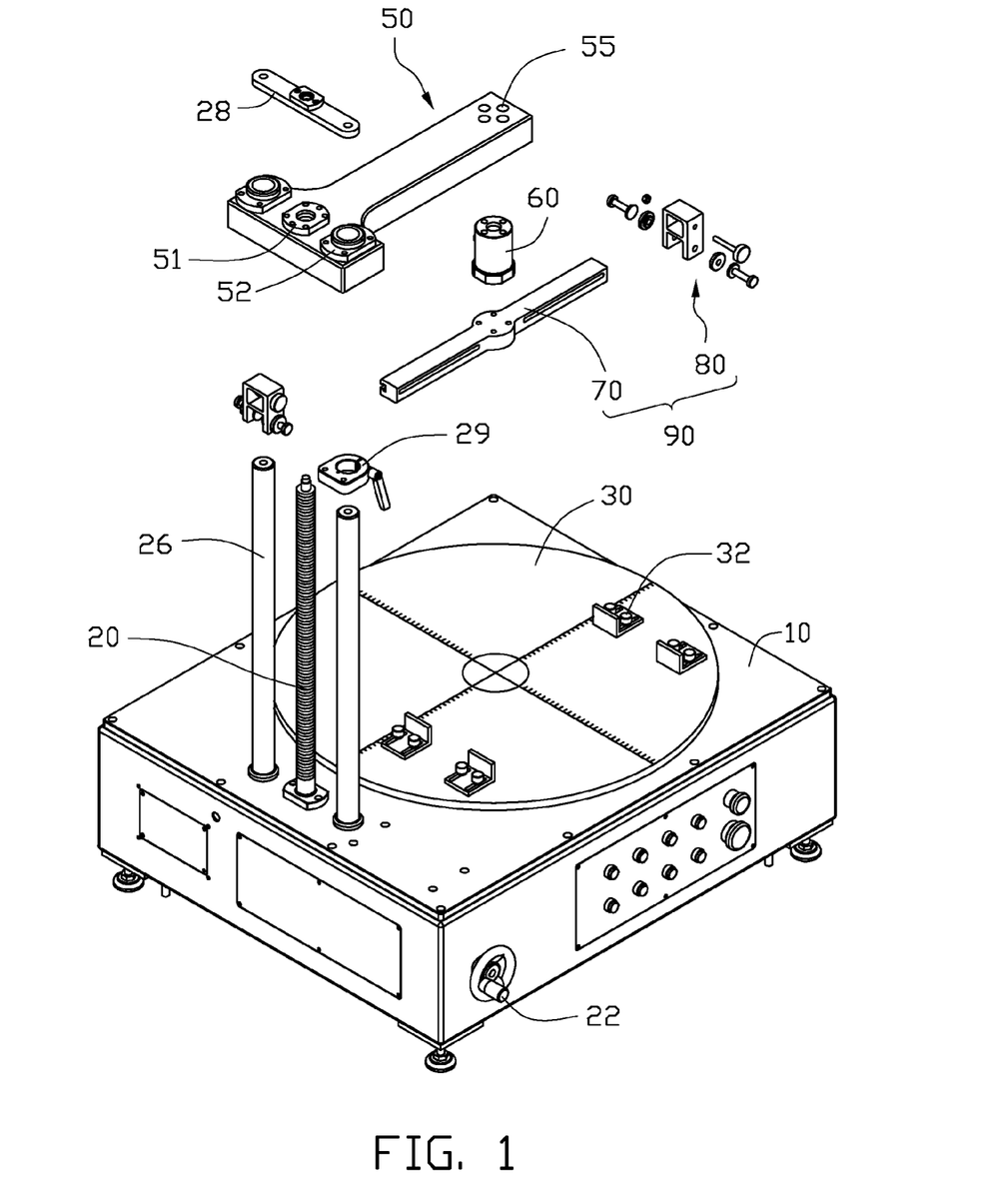
FIG. 1 is an exploded, isometric view of an embodiment of a stress test apparatus.
Figure 9:
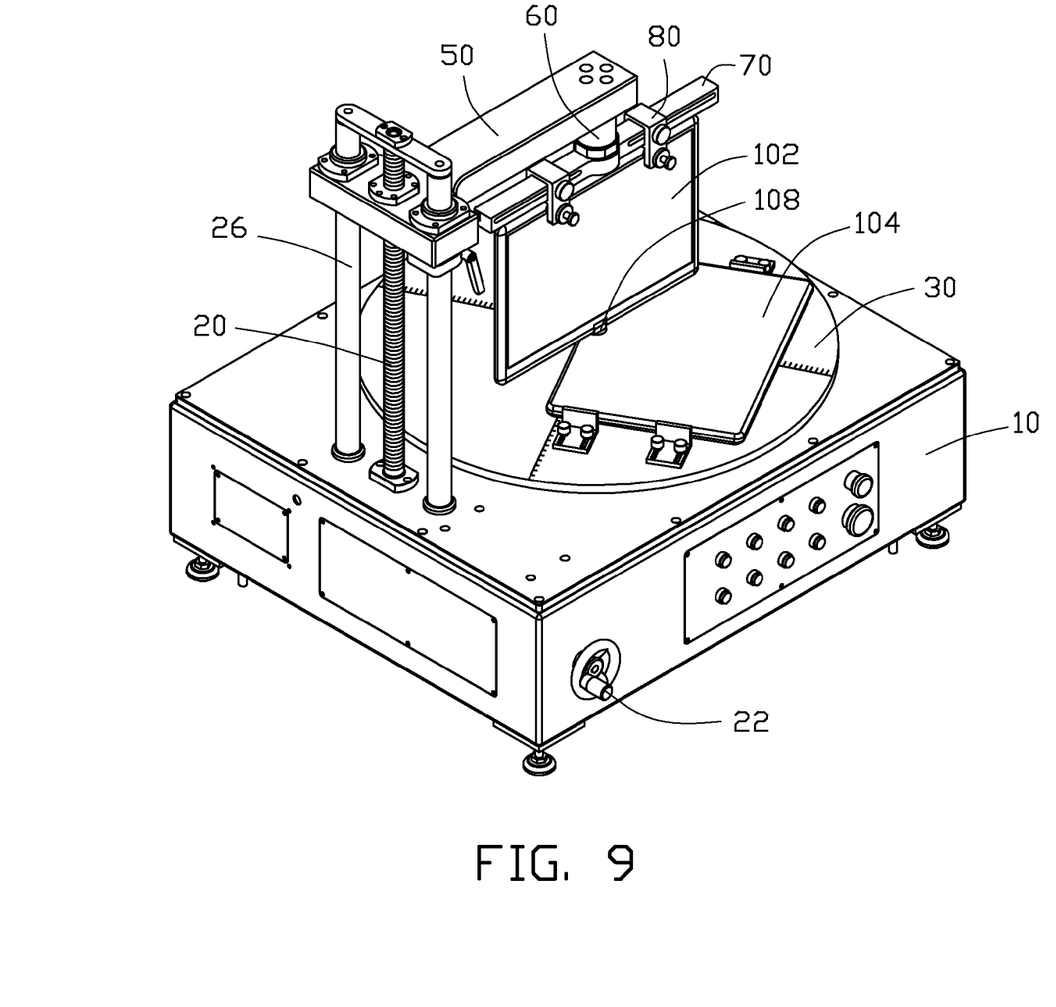
FIG. 9 is a testing state of FIG. 8.

Referring to FIG. 1 and FIG. 9, one embodiment of a stress test apparatus for an electronic device is used to perform a rotation stress test to a hinge of an electronic device 100. The stress test apparatus includes a console 10, a rotary table 30, a lifting pole 20, two guiding poles 26 positioned substantially parallel to the lifting pole 20, a traversing arm 50, a torque sensor 60 and a securing fixture 90.

In one embodiment, the rotary table 30 is rotatably installed on the console 10. The rotary table 30 rotates relative to the console 10 through a rotation motor (not shown). A coordinate axis with a central point is marked on the rotary table 30. Two pairs of L-shaped retainers 32 are located on the rotary table 30 to retain the electronic device 100 in position during testing. Each pair of retainers 32 are movably mounted to the rotary table 30.

Figure 2:
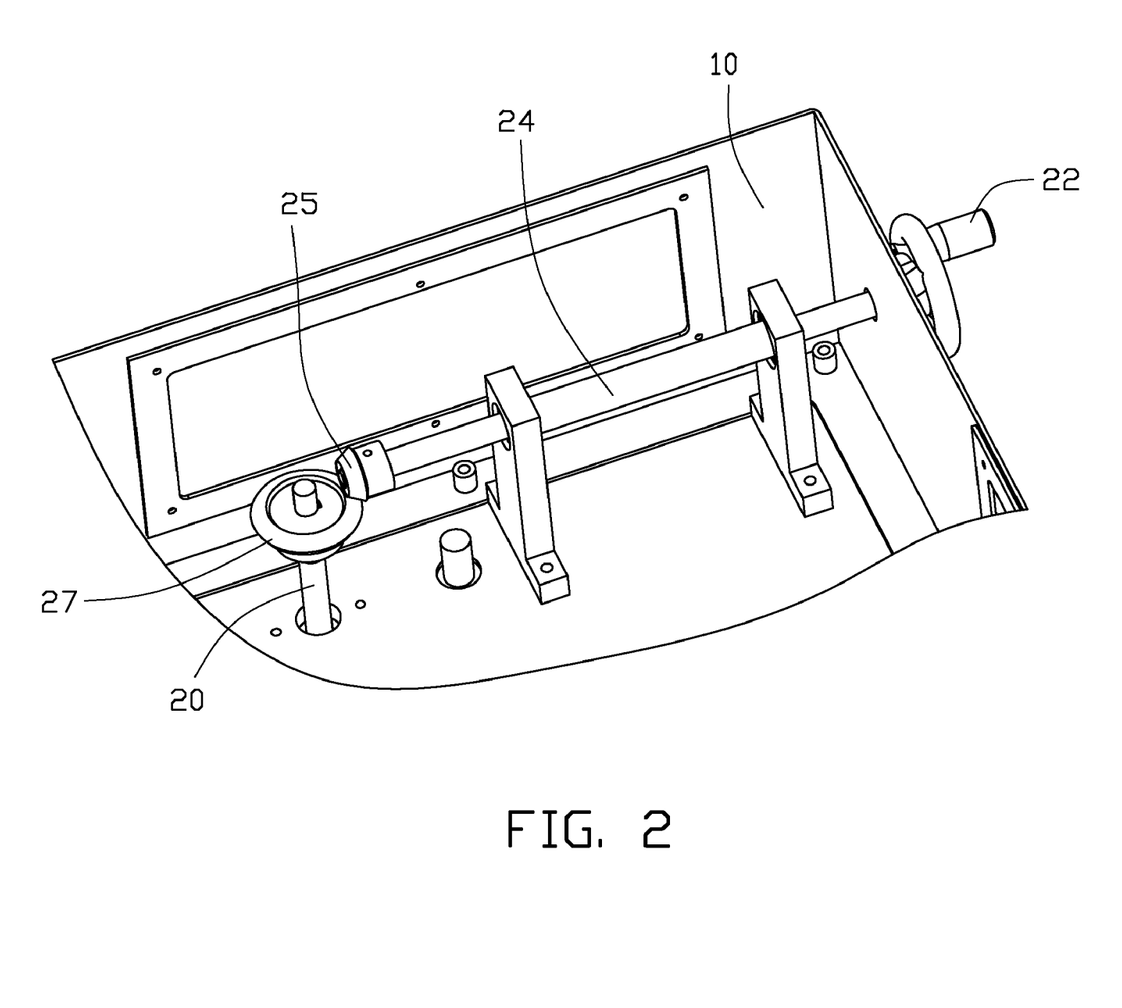
FIG. 2 is a partial, view of a console of FIG. 1, but shown from another aspect.

Referring to FIG. 2, an operating pole 24 is mounted to the console 10. A driving gear 25 is located on a distal end of the operating pole 24. A crank wheel 22 is attached to the operating pole 24 on the outside of the console 10.

The lifting pole 20 is located substantially perpendicular to the rotary table 30. A driven gear 27 is located at a lower portion of the lifting pole 20 to engage with the driving gear 27. Thus, a rotation about a horizontal axis of the operating pole 24 results in a rotation about a vertical axis of the lifting pole 20 through engagement of the driving gear 25 and the driven gear 27. The lifting pole 20 has external threads. The two guiding poles 26 mount to two opposite sides of the lifting pole 20.

The traversing arm 50 (see FIG. 1) is T-shaped. The traversing arm 50 has a screw 51 and two liner bearings 52. The screw 51 has internal threads to engage with the external threads of the lifting pole 20. The two liner bearings 52 are attached to the two guiding pole 26. The traversing arm 50 may be raised or lowered by rotating the lifting pole 20. A locater 29 attached to one of the guiding poles 20 to lock the traversing arm 50 into position. A stopper 28 is located on distal ends of the lifting pole 20 and the guiding poles 26. A plurality of mounting holes 55 is defined in the traversing arm 50 to secure the torque sensor 60.

Figure 3:
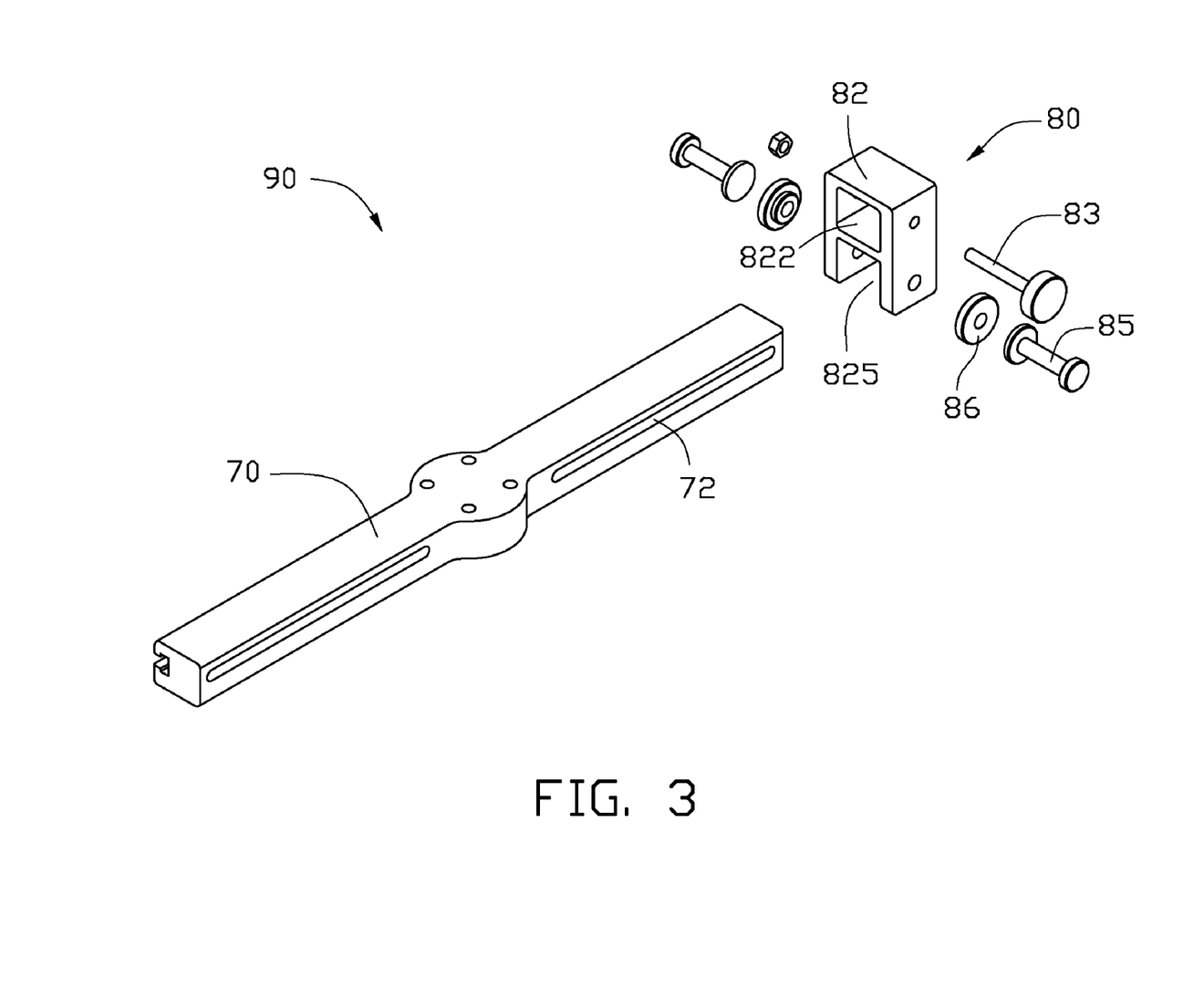
FIG. 3 is an enlarged view of a securing fixture of FIG. 1.

Referring to FIG. 3, the securing fixture 90 includes a holding rod 70 and two fasteners 80 (only one is shown in FIG. 3). The torque sensor 60 is located at a middle portion of the holding rod 70. The two fasteners 80 are located on two opposite sides of the torque sensor 60. Two traversing guiding slots 72 are defined in the holding rod 70.

Each fastener 80 includes a main body 82, a locking post 83 and a pair of adjusting bars 85. The main body 82 includes a guiding portion 822 and a U-shaped clamping portion 825. The holding rod 70 can extend through the guiding portion 822. The locking post 83 can extend through the guiding portion 822 and the corresponding guiding slot 72 for adjusting a position of the main body 80 on the holding rod 70. The adjusting bars 85 are located on opposite sides of the clamping portion 825 for clamping the electronic device 100. Two gaskets 86 are positioned between the two adjusting bars 85.

Figure 4:
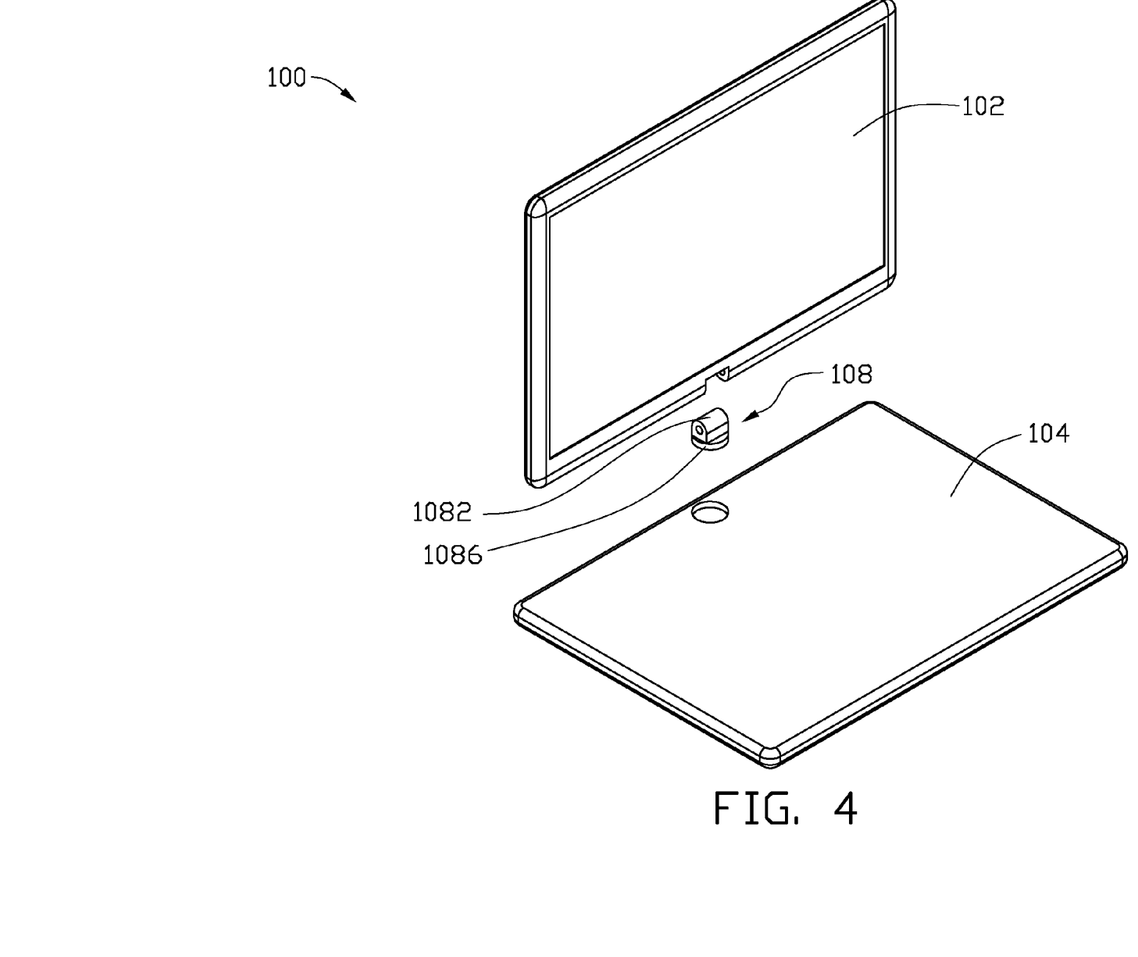
FIG. 4 is a partially exploded view of an electronic device according to one embodiment.

Referring to FIG. 4, the electronic device 100 may be a notebook computer. The electronic device 100 includes a top portion 102, a bottom portion 104 and a hinge 108 located between the top portion 102 and the bottom portion104. The hinge 108 includes a top hinge portion 1082 fixed to the top portion 102 and a bottom hinge portion 1086 fixed to the bottom portion104. The top hinge portion 1082 can rotate horizontally relative to the bottom hinge portion 1086.

Figure 5:
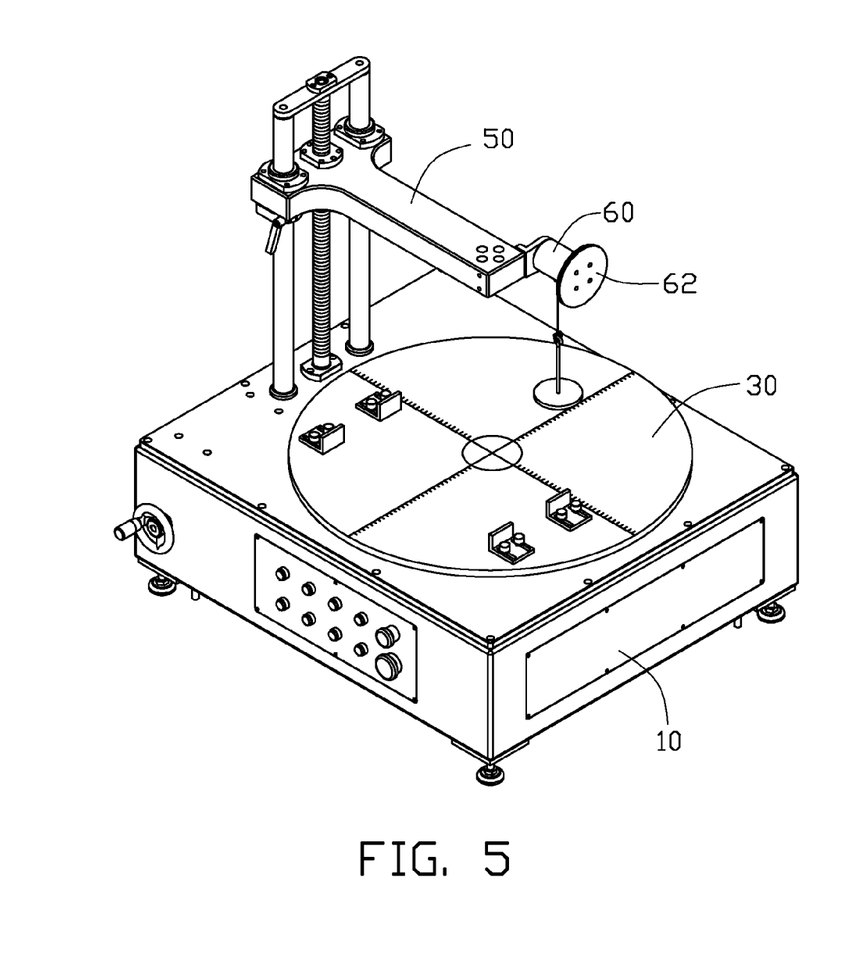
FIG. 5 shows one working state of a torque sensor according to one embodiment.

Referring to FIG. 5, to calibrate the torque sensor 60, the traversing arm 50 mounts to the lifting pole 20 and supported by the guiding poles 26. The stopper 28 is fixed on the distal ends of the lifting pole 20 and the guiding poles 26. The torque sensor 60 is horizontally fixed to the traversing arm 50. A calibration device 62 is mounted to the torque sensor 60 to calibrate the torque sensor 60.

Figure 6:
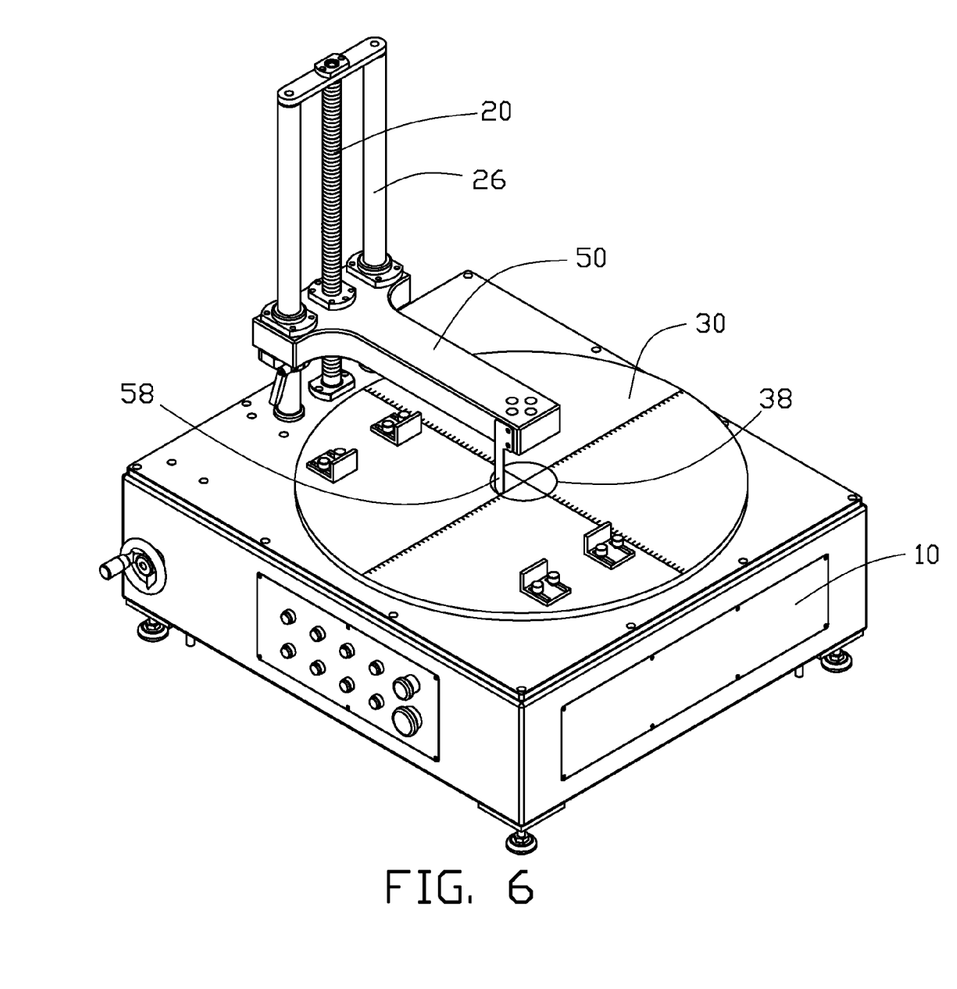
FIG. 6 shows one working state of a rotary table of the stress test apparatus according to one embodiment.

Referring to FIG. 6, to calibrate the rotary table 30, a locating pin 58 vertically attaches to an end of the traversing arm 50. A position of the rotary table 30 is adjusted to make the locating pin 58 point towards the angle index 38 when the rotary table 30 is rotated.

Figure 7:
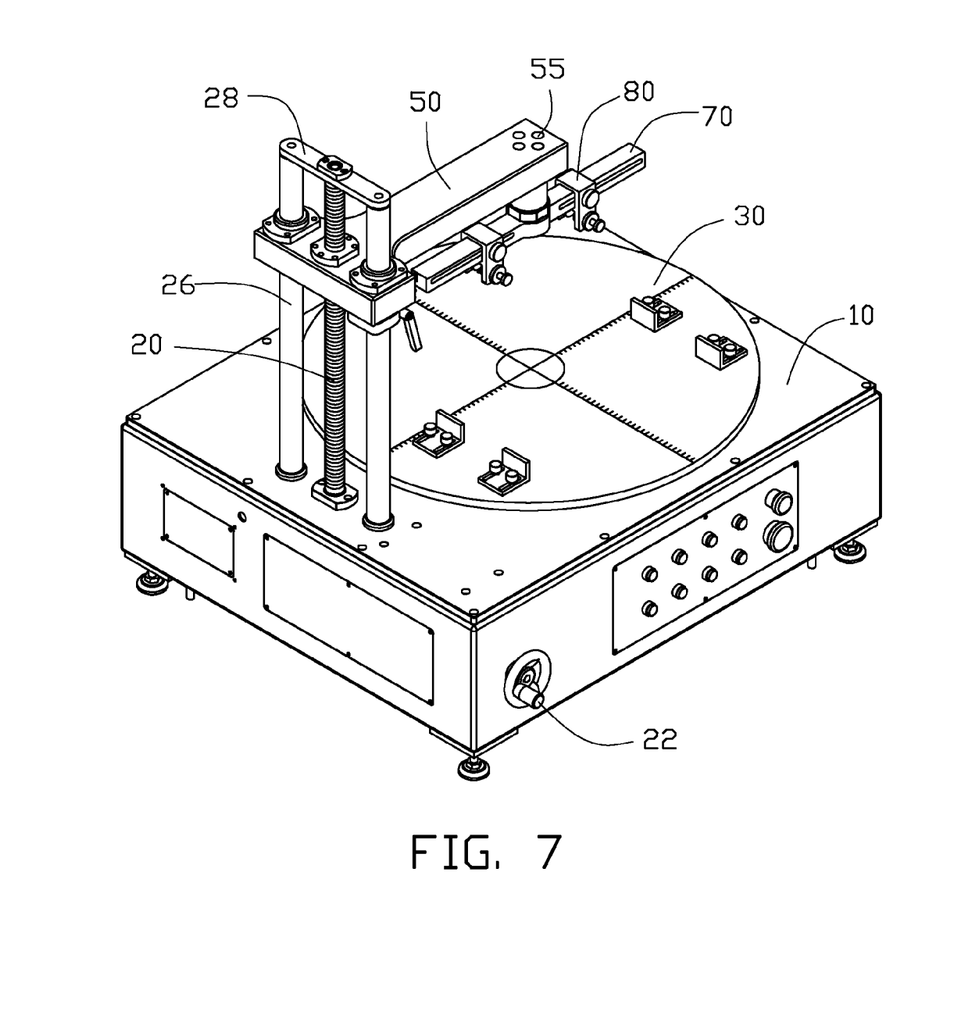
FIG. 7 is an assembled view of FIG. 1.

Referring to FIG. 7, during assembling the securing fixture 90 and the torque sensor 60 is fixed to the traversing arm 50. The torque sensor 60 is fixed to the middle portion of the holding rod 70. The two fasteners 80 are installed on the holding rod 70. Each locking post 83 extends through the corresponding guiding slot 72. The adjusting bars 85 are installed on the clamping portion 825 of the main body 82.

Figure 8:
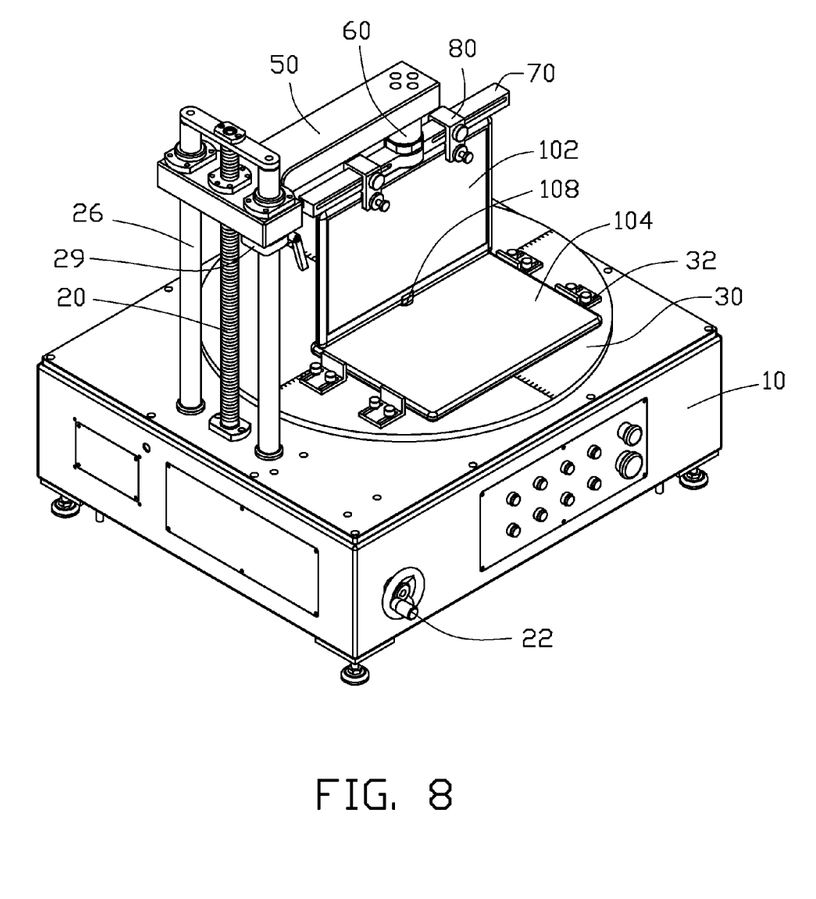
FIG. 8 is similar to FIG. 7, but with the electronic device fixed to the stress test apparatus.

Referring to FIG. 8, during assembling the electronic device 100, the electronic device 100 is positioned on the console 30 with the hinge 108 aligns with the central point of the rotary table 30. The bottom portion 104 of the electronic device 100 is clasped by the retainers 32 and held in a stationary position. The height of the traversing arm 50 is adjusted by rotating the crank wheel 22. The top portion 102 of the electronic device 100 is clasped securely by the fasteners 80.

Referring to FIG. 9, during testing the electronic device 100, the bottom portion 104 clasped to the rotary table 30 is rotated back and forth a number of times alternatively. The top portion 102 fixed to the holding rod 70 remains stationary.

Due to resistance caused by friction between the top hinge portion 1082 and the bottom hinge portion 1086, the torque sensor 60 can detect a torque value of the hinge 108. A performance of the hinge 108 of the electronic device 100 may then be received through changes of the torque value during testing.

It is also to be understood, that even though numerous characteristics and advantages have been set forth in the foregoing description of preferred embodiments, together with details of the structures and functions of the preferred embodiments, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. A stress test apparatus for testing a hinge between a top portion and a bottom portion of an electronic device, the stress test apparatus comprising:
   a console;
   a rotary table located on the console for retaining the bottom portion;
   a lifting pole extending from the console;
   a traversing arm, the traversing arm slidably attached to the lifting pole to adjust a height of the traversing arm relative to the console;
   a securing fixture clasping the top portion of the electronic device; and
   a torque sensor fixed between the traversing arm and the securing fixture;
   wherein the bottom portion is capable of being rotated relative to the top portion with rotation of the rotary table, and the torque sensor is capable of detecting torque needed for rotating the top portion relative to the bottom portion.

2. The stress test apparatus of claim 1 further comprising a guiding pole substantially parallel to the lifting pole, and the traversing arm is slidably installed on the guiding pole to prevent the traversing arm from rotating relative to the lifting pole.

3. The stress test apparatus of claim 2, wherein a locater is held on the guiding pole for blocking the traversing arm from moving out of the guiding pole.

4. The stress test apparatus of claim 1, wherein the lifting pole has an external thread, and the traversing arm has a screw with an internal thread to engage with the lifting pole.

5. The stress test apparatus of claim 4 further comprising an operating pole substantially perpendicular to the lifting pole, and the operating pole has a driving gear, and the lifting pole has a driven gear to mesh with the driving gear.

6. The stress test apparatus of claim 1, wherein the securing fixture comprising a holding rod and two fasteners slidably mounted to the holding rod for clasping the top portion of the electronic device, and the torque sensor is fixed to a middle portion of the holding rod.

7. The stress test apparatus of claim 6, wherein two guiding slots is defined in the holding rod, and each of the two fasteners comprises a locking post extending through each of the two guiding slots.

8. The stress test apparatus of claim 7, wherein each of the two fasteners comprises a main body, the main body has a guiding portion attached to the holding rod, each of the two locking posts extends through each of the two guiding portions.

9. The stress test apparatus of claim 6, wherein each of the two fasteners comprises a main body and a pair of adjusting bars, and each main body has a U-shaped clamping portion for clasping the top portion of the electronic device.

10. The stress test apparatus of claim 1, wherein a pair of L-shaped retainers is located on the rotary table, and the pair of L-shaped retainers is slidably mounted to the rotary table to clasp the bottom portion of the electronic device.

11. A stress test apparatus for testing a hinge between a top portion and a bottom portion of an electronic device, the stress test apparatus comprising:
    a console;
    a rotary table located on the console for retaining the bottom portion;
    a lifting pole extending from the console;
    a traversing arm, the traversing arm attached to the lifting pole, the traversing arm located substantially perpendicular to the lifting pole and substantially parallel to the rotary table;
    a securing fixture connected to the torque sensor and clasping the top portion of the electronic device; and
    a torque sensor fixed between the traversing arm and the securing fixture;
    wherein the bottom portion is capable of being rotated relative to the top portion with rotation of the rotary table, and the torque sensor is capable of detecting torque needed for rotating the top portion relative to the bottom portion.

12. The stress test apparatus of claim 11 further comprising a guiding pole substantially parallel to the lifting pole, and the traversing arm is slidably installed to the guiding pole to prevent the traversing arm from rotating relative to the lifting pole.

13. The stress test apparatus of claim 12, wherein a locater is held on the guiding pole for blocking the traversing arm from moving out of the guiding pole.

14. The stress test apparatus of claim 11, wherein the lifting pole has an external thread, and the traversing arm has a screw with an internal thread to engage with the lifting pole.

15. The stress test apparatus of claim 14 further comprising an operating pole substantially perpendicular to the lifting pole, and the operating pole has a driving gear, and the lifting pole has a driven gear to mesh with the driving gear.

16. The stress test apparatus of claim 11, wherein the securing fixture comprising a holding rod and two fasteners slidably mounted to the holding rod for clasping the top portion of the electronic device, and the torque sensor is fixed on a middle portion of the holding rod.

17. The stress test apparatus of claim 16, wherein two guiding slots is defined in the holding rod, and each of the two fasteners comprises a locking post extending through each of the two guiding slots.

18. The stress test apparatus of claim 17, wherein each of the two fasteners comprises a main body, the main body has a guiding portion attached to the holding rod, each of the two locking posts extends through each of the two guiding portions.

19. The stress test apparatus of claim 16, wherein each of the two fasteners comprises a main body and a pair of adjusting bars, and each main body has a U-shaped clamping portion for clasping the top portion of the electronic device.

20. The stress test apparatus of claim 11, wherein a pair of L-shaped retainers is located on the rotary table, and the pair of L-shaped retainers is slidably mounted to the rotary table to clasp the bottom portion of the electronic device.

* * * * *

UNITED STATES PATENT AND TRADEMARK OFFICE
CERTIFICATE OF CORRECTION

PATENT NO. : 8,291,774 B2 Page 1 of 1
APPLICATION NO. : 12/889555
DATED : October 23, 2012
INVENTOR(S) : Teng-Tsung Huang et al.

It is certified that error appears in the above-identified patent and that said Letters Patent is hereby corrected as shown below:

Title Page insert Item (30) "Foreign Application Priority Data":

-- (30)   Foreign Application Priority Data

May 12, 2010   (CN) .........................201010171439.2 --

Signed and Sealed this
Fifteenth Day of October, 2013

Teresa Stanek Rea
*Deputy Director of the United States Patent and Trademark Office*